US00PP33351P2

(12) United States Plant Patent
Olesen

(10) Patent No.: US PP33,351 P2
(45) Date of Patent: Aug. 17, 2021

(54) ***ROSA* HYBRID NAMED 'POULPAH103'**

(50) Latin Name: *Rosa hybrida*
Varietal Denomination: Poulpah103

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 16/873,996

(22) Filed: Sep. 3, 2020

(51) Int. Cl.
*A01H 6/74* (2018.01)
*A01H 5/02* (2018.01)

(52) U.S. Cl.
USPC ..... Plt./121

(58) Field of Classification Search
USPC ..... Plt./121
See application file for complete search history.

(56) References Cited

PUBLICATIONS http://www.poulsenroser.com/assortment/rose-collections/patiohit/dafne.aspx 2018.*
https://www.poulsenroser.dk/en/roses/ShowProduct/62453 2018.*

* cited by examiner

*Primary Examiner* — Annette H Para

(57) ABSTRACT

A new garden rose plant of the Miniature class which has abundant, pink flowers and attractive foliage. This new and distinct variety has shown to be uniform and stable in the resulting generations from asexual propagation.

1 Drawing Sheet

Botanical designation: *Rosa hybrida.*
Variety denomination: 'Poulpah103'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2011 and the resulting seeds were planted in a controlled environment in Fredensborg, Denmark. The new variety, named 'Poulpah103', originated as a single seedling from the stated cross.

The new variety may be distinguished from its male pollen parent and female seed parent primarily by the following characteristics. The male pollen parent plant has near white flowers while the new variety has pink flowers. The female seed parent plant has red flowers while the new variety has pink flowers.

The objective of the hybridization of this rose variety was to create a new and distinct variety with unique qualities, such as:

1. Uniform and abundant pink flowers;
2. Vigorous, but compact growth when propagated on its own roots;
3. Exceptional disease resistance.

This combination of qualities is not present in previously available commercial cultivars of this type, known to the inventor, and distinguish 'Poulpah103' from all other varieties of which we are aware.

As part of the rose development program, Mogens N. Olesen germinated the seeds from the aforementioned hybridization during winter of 2011 and conducted evaluations on the resulting seedlings in a controlled environment in Fredensborg, Denmark. 'Poulpah103' was selected in the spring of 2012 by the inventor as a single plant from the progeny of the aforementioned hybridization.

Asexual reproduction of 'Poulpah103' by rooted cuttings was first done by Mogens N. Olesen in the nursery in Fredensborg, Denmark in July, 2012. This initial and other subsequent asexual propagations conducted in controlled environments have demonstrated that the characteristics of 'Poulpah103' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpah103'.

Specifically illustrated in the drawing are a cluster of open flowers and flower buds on the branch, an open flower viewed from above, flower petals and sepals detached revealing receptacle, bare stems, mature leaves, and juvenile leaves exhibiting anthocyanin. Plants shown are 2 years of age.

DETAILED DESCRIPTION OF THE VARIETY

The following is a description of 'Poulpah103', as observed in its growth in a field nursery in Linn County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulpah033', U.S. Plant Pat. No. 17,509 are compared to 'Poulpah103' in Chart 1.

CHART 1

| | 'Poulpah103' | 'Poulpah033' |
|---|---|---|
| Petal Count | 80 | 40 |
| Flower Diameter | 65 mm | 80 mm |
| General Tonality of Flower Color | Red-Purple Group 67C with other intonations of Red-Purple Group N66B | Red-Purple Group N57A and N66A |

FLOWER AND FLOWER BUD

Blooming habit: Continuous.

Flower bud:

*Size.*—Upon opening, 26 mm in length from base of receptacle to end of bud. Bud diameter is 14 mm.

*Bud form.*—Urceolate.

*Bud color.*—As sepals divide petals are Red-Purple Group 60C and 60D.

*Sepal inner surface.*—Color: Yellow-Green Group 144D with intonations of Greyed-Red Group 179A. Surface: Lightly pubescent.

*Sepal outer surface.*—Color: Yellow-Green Group 144A with intonations of Greyed-Purple Group 183B. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—20 mm long, 11 mm wide.

*Receptacle.*—Texture: Smooth. Size: 6 mm in height, 10 mm wide. Color: Yellow-Green Group 144A with intonations of Greyed-Purple Group 183D. Shape: Funnel.

*Pedicel.*—Surface: Smooth. Length: 30 mm. Diameter: 2 mm on average. Color: Yellow-Green Group 144A with intonations of Greyed-Purple Group 183C. Strength: Strong.

*Peduncle.*—Length: 2 to 3 cm. Diameter: About 3 mm. Color: Yellow-Green Group 144A with intonations of Greyed-Purple Group 183C. Texture: Smooth.

Flower bud development: Flower buds are borne in clusters of 7 to 10 flower buds per stem. Development as a panicle.

Flower bloom:

*Fragrance.*—Strong perfume.

*Duration.*—The blooms have a duration on the plant of approximately 15 days. Petals fall cleanly away from plant after flowers have fully matured.

*Size.*—Flower diameter is 65 mm when open. Flower depth is 25 mm.

*Flower shape.*—Rosette.

*Shape of flower, side view.*—The upper portion is convex. The lower portion is concave.

Petalage: Under normal conditions, flowers have about 80 petals.

General tonality of flower: Open flowers are Red-Purple Group 67C with other intonations of Red-Purple Group N66B.

Petal color:

*Upon opening, outer petals.*—Upper surface: Red-Purple Group 67C splashed with intonations of Red-Purple Group 67A. Lower surface: Red-Purple Group 68B splashed with Red-Purple Group 69B.

*Upon opening, inner petals.*—Upper surface: Red-Purple Group N57C. Lower surface: Red-Purple Group 62A, splashed with Red-Purple Group 69B.

*Basal petal spots, upon opening.*—Upper surface: Yellow Group 4C. Lower surface: Yellow Group 4D.

*After opening, outer petals.*—Upper surface: Red-Purple Group 75A splashed with Red-Purple Group 68A. Lower surface: Red-Purple Group 73A splashed with Red-Purple Group 73D.

*After opening, inner petals.*—Upper surface: Red-Purple Group 75A splashed with Red-Purple Group 68A. Lower surface: Red-Purple Group 73A splashed with Red-Purple Group 73D.

*Basal petal spots, after opening.*—Upper surface: White Group 155A. Lower surface: White Group 155A.

Petals:

*Petal reflex.*—Moderate to strong.

*Margin.*—Entire and uniform. Moderate undulations.

*Shape.*—Broad and elliptic. Apex shape: Rounded. Base shape: Acute.

*Size.*—35 mm (l)×42 mm (w).

*Texture.*—Smooth.

*Thickness.*—Average.

Reproductive flower parts:

*Pollen.*—None observed.

*Anthers.*—Size: 2 mm in length. Color: Yellow Group 4D. Quantity: 35 on average.

*Filaments.*—Color: Yellow Group 9B. Length: 3 mm.

*Pistils.*—Length: 6 mm. Quantity: 24 on average.

*Stigmas.*—Color: Green-White Group 157A.

*Styles.*—Color: Green-White Group 157A.

*Location of stigmas.*—Level in location relative to the length of the filaments and the height of the anthers.

*Hips.*—None Observed.

PLANT

Plant growth: Upright and compact. Plants are about 42 cm in height, and 35 cm wide.

Stems:

*Color of juvenile growth.*—Yellow-Green Group 144A with intonations of Greyed-Purple Group 183C.

*Color of mature growth.*—Yellow-Green Group 144A.

*Length.*—Canes are about 20 cm from the base of the plant to the flowering portion.

*Diameter.*—About 6 mm.

*Internodes.*—On mature canes about 30 mm between nodes.

*Surface texture.*—Young wood: Smooth. Older wood: Smooth.

Long prickles:

*Incidence.*—3 prickles per 10 cm of stem.

*Size.*—Average length of prickles on mature stems is 9 mm.

*Shape.*—Upper portion is linear. Lower portion is concave.

*Color.*—Juvenile prickles: Orange-Red Group N34C and Greyed-Yellow Group 160 162B. Mature prickles: Greyed-Red Group 180B.

Plant foliage:

*Compound leaf.*—105 mm (l)×76 mm (w).

*Quantity.*—3 leaves per 10 cm of stem on average.

*Leaf bearing angle to the stem.*—45 degrees.

*Color of juvenile foliage*.—Upper side: Yellow-Green Group 144A with intonations of Greyed-Purple Group 183A at the margins. Lower side: Yellow-Green Group 144B with intonations of Greyed-Purple Group 183A.

*Color of mature foliage*.—Upper side: Yellow-Green Group 146A. Lower side: Yellow-Green Group 147B.

Plant leaves and leaflets:

*Stipules*.—Size: 23 mm long, 3 mm wide. Quantity: 2 per compound leaf. Shape: Linear, slightly broad based with outward extending apices. Margins: Finely serrated. Color:

*Petiole*.—Length: 30 mm. Diameter: 2 mm. Upper surface color: Yellow-Green Group 144A. Lower surface color: Yellow-Green Group 144A.

*Rachis*.—Length: 43 mm. Upper surface color: Yellow-Green Group 144B. Lower surface color: Yellow-Green Group 144A.

*Leaflet*.—Quantity: Normally 5 leaflets. Margins: Serrated. Size: Terminal leaflets are about 43 mm long, 38 mm wide. Shape: Generally elliptical. Base: Rounded. Apex: Mucronate. Texture: Smooth. Thickness: Average. Arrangement: Odd pinnate. Venation: Reticulate. Glossiness: Very glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Miniature rose class named 'Poulpah103', substantially as illustrated and described herein, due to its abundant pink flowers, disease resistance, and extended period of bloom.

* * * * *

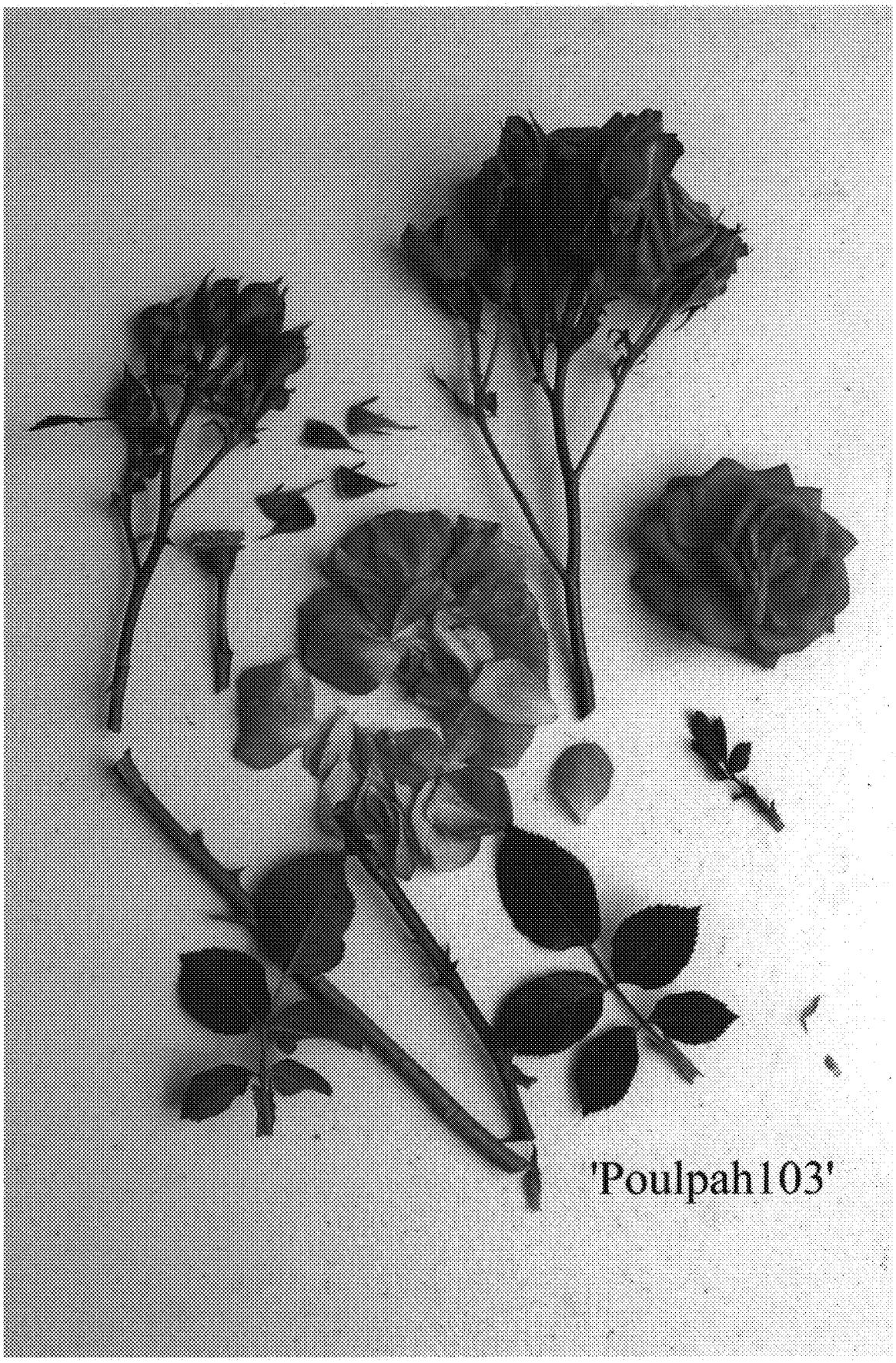
'Poulpah103'